United States Patent
Dai et al.

(10) Patent No.: US 9,745,254 B2
(45) Date of Patent: Aug. 29, 2017

(54) TWO-STEP AND ONE-POT PROCESSES FOR PREPARATION OF ALIPHATIC DIISOCYANATES

(71) Applicant: Great Eastern Resins Industrial Co., Ltd., Taichung (TW)

(72) Inventors: Shenghong A. Dai, Taichung (TW); Wei Hsing Lin, Taichung (TW); Yi-Syuan Guo, Taichung (TW)

(73) Assignee: Great Eastern Resins Industrial Co., Ltd. (TW)

( * ) Notice: Subject to any disclaimer, the term of this patent is extended or adjusted under 35 U.S.C. 154(b) by 0 days.

(21) Appl. No.: 15/000,285

(22) Filed: Jan. 19, 2016

(65) Prior Publication Data

US 2017/0015621 A1  Jan. 19, 2017

(30) Foreign Application Priority Data

Jul. 17, 2015 (TW) .............................. 104123293 A

(51) Int. Cl.
| | |
|---|---|
| C07C 261/00 | (2006.01) |
| C07C 269/00 | (2006.01) |
| C07C 271/00 | (2006.01) |
| C07C 263/04 | (2006.01) |
| C07C 269/04 | (2006.01) |

(52) U.S. Cl.
CPC .......... *C07C 263/04* (2013.01); *C07C 269/04* (2013.01)

(58) Field of Classification Search
CPC .............................. C07C 263/04; C07C 269/04
See application file for complete search history.

(56) References Cited

U.S. PATENT DOCUMENTS

| | | | | |
|---|---|---|---|---|
| 3,919,279 A * | 11/1975 | Rosenthal | ............. | C07C 263/04 560/24 |
| 4,659,845 A * | 4/1987 | Rivetti | ................... | C07C 263/04 549/438 |
| 2003/0125579 A1 | 7/2003 | Yoshida et al. | | |
| 2012/0245377 A1* | 9/2012 | Bock | ..................... | C07C 263/04 560/345 |

FOREIGN PATENT DOCUMENTS

| | | |
|---|---|---|
| CA | 1108174 A | 9/1981 |
| CN | 1281580 C | 10/2006 |
| EP | 0327231 A1 | 8/1989 |
| EP | 0408277 A2 | 1/1991 |
| EP | 2275405 A1 | 1/2011 |
| JP | S60226852 A | 11/1985 |
| TW | 201313664 A | 4/2013 |

OTHER PUBLICATIONS

Sharma et al. (Synthesis and characterization of alternating poly(amide urethane)s from eplison-caprolactam, amino alcohols, and diphenyl carbonate, Polymer 45, pp. 5427-5440, published 2004).*
Cenini, S., et al., "Ruthenium Carbonyl Catalyzed Reductive Carbonylation of Aromatic Nitro Compounds. A Selective Route to Carbamates", J.Org. Chem., 1988, vol. 53, No. 6, pp. 1243-1250.
Chen, H-Y., et al., "Synthesis and trans-ureation of N, N'-diphenyl-4, 4'-methylenediphenylene biscarbamate with diamines: a non-isocyanate route (NIR) to polyureas", J Polym. Res., 2012, vol. 19, pp. 1-11.
Eckert, H., et al., "Triphosgene, a Crystalline Phosgene Substitute", Abgew. Chem. Int. Ed. Engl., 1987, vol. 26, No. 9, pp. 894-895.
English Translation of Taiwanese Search Report for Application No. 104123293, dated Mar. 10, 2016.
Shinsuke, F., et al., "A Novel Catalytic Synthesis of Carbatmates by the Oxidative Alkoxycarbonylation of Amines in the Prescence of Platinum Group Metal and Alkali Metal Halide or Onium Halide", J. Org. Chem., 1984, vol. 49, No. 8, pp. 1458-1460.
Taiwanese Office Action for application 104123293, dated Mar. 15, 2016.
Taiwanese Search Report for application 104123293, dated Mar. 15, 2016.

* cited by examiner

*Primary Examiner* — Yevegeny Valenrod
*Assistant Examiner* — Blaine G Doletski
(74) *Attorney, Agent, or Firm* — Drinker Biddle & Reath LLP

(57) ABSTRACT

The present invention relates to using a two-step (thermolysis) or one-pot process to prepare aliphatic diisocyanates from aliphatic diamines and diaryl carbonates. Polyisocyanates can also be prepared from polyamines and diaryl carbonates. The present synthetic processes do not apply phosgene or highly toxic reagents and chloro-solvents during the entire procedure.

28 Claims, No Drawings

TWO-STEP AND ONE-POT PROCESSES FOR PREPARATION OF ALIPHATIC DIISOCYANATES

CROSS-REFERENCE TO RELATED APPLICATIONS

This application claims the benefit of Taiwanese Application No. 104123293, filed Jul. 17, 2015, which is incorporated herein by reference in its entirety.

FIELD OF THE INVENTION

The present invention relates to using a two-step (thermolysis) or one-pot process to prepare aliphatic diisocyanates from aliphatic diamines and diaryl carbonates. Polyisocyanates can also be prepared from polyamines and diaryl carbonates. Unlike the common phosgene processes for the production of aliphatic diisocyanates known in the industry, the present synthetic processes do not apply phosgene, highly toxic reagents or chloro-solvents during the entire procedure.

DESCRIPTION OF THE RELATED ART

Isocyanates are widely applied in industry, such as production of polymers, in particular organic diarylisocyanates and polyarylisocyanates for the production of polyurethane, polyurethane/urea, polyurea and related polymers.

Aryl polyisocyanates, as well as aliphatic polyisocyanates, can be used in various applications. Aryl diisocyanates, such as 2,4-toluenediisocyanate and 2,6-toluenediisocyanate (TDI) and 4,4'-diphenylmethanediisocyanate (MDI), are employed in the majority of isocyanate products (>90%) out of consideration for cost, performance, reaction rate and utility in the production of formed polyurethane and bulk foam. Nevertheless, global production of MDI and TDI, amounting to over 0.35 million tons per year, is still dominated by phosgene processes. In recent years, it has been found that products made from aliphatic diisocyanates (ADIs) are superior to those made from aromatic diisocyanates in terms of resistance to yellowing, so there is growing interest in aliphatic diisocyanates (ADIs) and their potential applications. Since the phosgene gas used in the phosgene processes is toxic and produces corrosive hydrogen chloride, people in the art seek green production processes for ADIs that do not employ phosgene so as to fulfill the requirements of public and environmental health and safety requirements in the workplace.

In view of the related references and patents in the art, six process routes, among others, have been developed for non-phosgene processes of preparing ADIs: solid phosgene, $CO_2$ process, dimethylcarbonate (DMC) process, CO carbonylation process (with metal catalysts), transesterification and pyrolysis.

(1) Solid Phosgene—Triphosgene Method

The research of Heiner Eckert et al. (Heiner Eckert, Barbara Forster. Triphosgene, a Crystalline Phosgene Substitute. *Angew. Chem. Int. Ed. Engl.* 1987; 26(9):894-5) in 1987 produced the triphosgene method to replace the phosgene process for the synthesis of hexamethylene diisocyanate (HDI) with the reagent bis(trichloromethyl)carbonate. The reaction scheme is shown below:

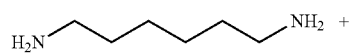

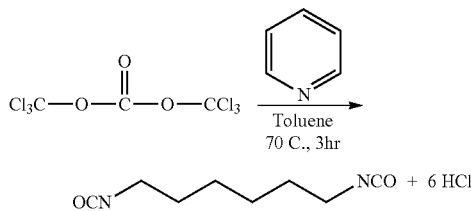

The reagent bis(trichloromethyl)carbonate is in a solid form and exhibits a higher melting point and a lower volatility (or vapor pressure), but has the same industrial disadvantage of creating vast amounts of gaseous hydrogen chloride during the reaction period, thereby leading to corrosive damage to equipment.

(2) CO Carbonylation Process—Carbonylation of Nitro-Compounds

In 1985, the research by Olin Corporation in the United States showed that nitro compounds can be directly converted to isocyanates by reduction in the presence of CO and catalysis of platinum and rhodium. The reaction scheme is shown below:

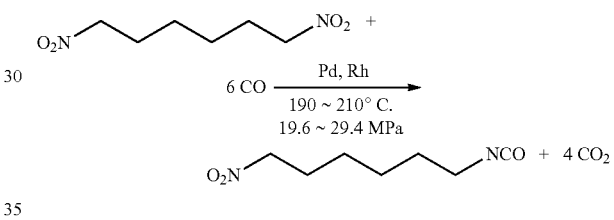

However, this method is rarely applied in industrial processes mainly because of overly low yield of isocyanates, harsh reaction conditions (high temperature and high pressure) and difficulty in the recovery of noble metal catalysts.

(3) CO Carbonylation Process—Oxidative Carbonylation of Primary Amine

In 1984, a patent owned by Asahi Chemical Ind. (Japan) (JP S60-226852) disclosed converting diamines, carbon monooxide and oxygen to HDI and water by catalysis of palladium. The reaction scheme is shown below:

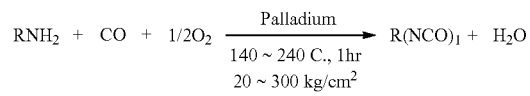

The recovery of noble metal catalysts used in the reaction is difficult and the byproduct $H_2O$ produced during production results in problems of lower yield of isocyanates and incomplete isolation of products from the bulk.

(4) Transesterification

In 1988, the patent developed by Thorpe D. of Imperial Chemical Industries (ICI) (England) (EP 0327231 A1) disclosed transesterification of aromatic diisocyanates, MDI, with an aliphatic diamine, hexanediamine (HDA), in a solvent of chlorobenzene, wherein the yield of the aliphatic diisocyanate, HDI, is about 40%. The reaction scheme is shown below:

$H_2N(CH_2)_6NH_2$ +

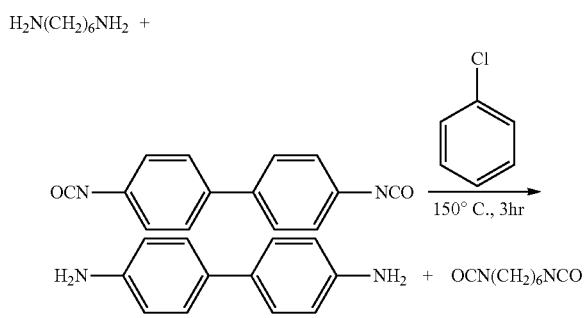

However, the yield is low and there is also a problem of incomplete isolation of the products from the bulk.

(5) $CO_2$-Carbonylation of Aliphatic Amines

In 1993, the patent by Mcghee William et al. of Monsanto (United States) (U.S. Pat. No. 5,451,697 A) disclosed reacting HDA and $CO_2$ by the catalysis of triethyleneamine (TEA) in a solvent of acetonitrile at 0° C. for 1.5 hours to synthesize ammonium urethane salts, followed by dehydration at −20° C. by using dehydrants such as sulfobenzoic acid anhydride (SBA) or phosphorus oxychloride ($POCl_3$) to produce HDI (yield of about 81%) and $H_2O$. The reaction scheme is shown below:

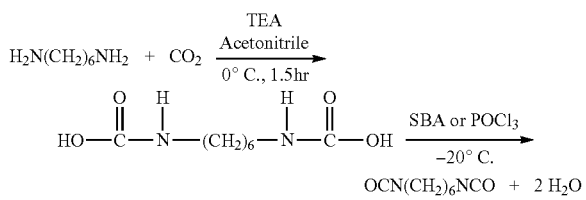

However, the reagents (dehydrants) used in the second step are still highly active chlorides, which produce environmental pollution and are difficult to isolate. In addition, if the $H_2O$ produced in the reaction cannot be effectively removed, it will react with the final product HDI, thereby decreasing product yield.

(6) Pyrolysis

Although the above-mentioned non-phosgene processes provide certain improvements over the traditional phosgene process, there are still problems such as low yield, low reaction rate, harsh reaction conditions (e.g., high temperature or pressure) or the need for noble metal catalysts. These significantly limit practicability and commercial applications. Given this, in the late 1980s, two-step non-phosgene processes were comprehensively studied, wherein the intermediate biscarbamates are synthesized followed by pyrolysis at a high temperature to form diisocyanates. Higher yield of diisocyanates can be achieved by pyrolysis of intermediate biscarbamates, and various types of biscarbamates can be synthesized based on the final product isocyanates. For example, the intermediate may comprise chlorosilylcarbamates, urea, N,N'-dimethyl hexane-1,6-diyldicarbarmate (HDU), etc. Among these, processes involving N,N'-dimethyl hexane-1,6-diyldicarbamate (HDU) provide more advantages and thus are widely studied.

(A) Chlorosilylcarbamate as an Intermediate

In 1976, a patent application of Union Carbide Corporation (United States) (CA 1108174 A2) disclosed a synthetic method comprising three steps: (a) reacting HDA, $CO_2$ and trimethylchlorosilane to form bis(trimethylsilyl) N,N'-hexylene biscarbamate and HCl; (b) reacting the biscarbamate with trichlorophenylsilane to replace the trimethylsilyl; and (c) adding $NH_3$ to neutralize HCl followed by pyrolysis at a high temperature to form HDI. The reaction scheme is shown below:

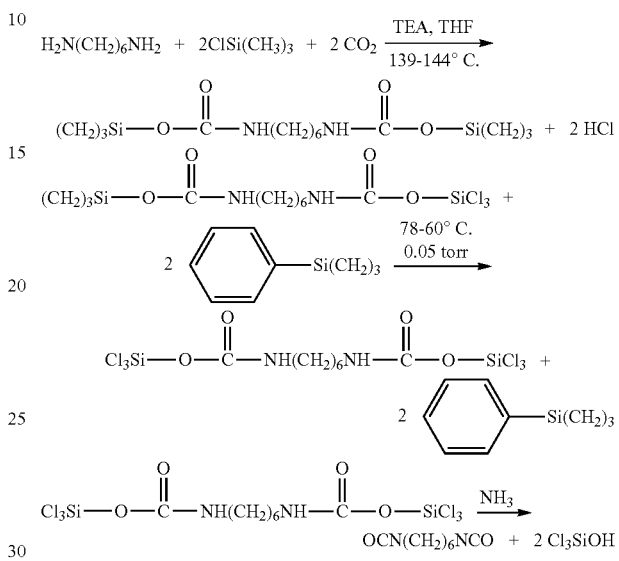

Although phosgene is not used in the method, HCl created in the method not only corrupts equipment but also reacts with HDI to form carbamoyl chloride. In addition, the byproducts, chlorosilanes, cause severe environmental pollution and incomplete separation from the product.

(B) Urea as an Intermediate

In 1989, a patent application of ARCO Chemical Technology, Inc. (United States) (EP 0408277 A2) disclosed a synthetic method comprising the following steps: (a) reacting HDA with isocyanic acid to form hexamethylenediurea; (b) reacting hexamethylenediurea with diethylamine to form hexamethylene bis(diethylurea); and (c) pyrolysis of hexamethylene bis(diethylurea) at a high temperature to form HDI. The reaction scheme is shown below:

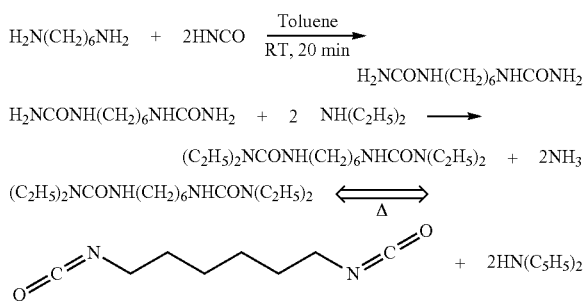

Nevertheless, the reagents are expensive and xylene and HNCO are toxic. In addition, the overall reaction rate is somewhat slow.

(C) N,N'-dimethyl hexane-1,6-diyldicarbamate (HDU) as an Intermediate

In view of different raw materials and reaction routes for synthesizing N,N'-dimethyl hexane-1,6-diyldicarbamate (HDU), the methods can be classified according to the following four types: reductive carbonylation of nitro compounds, oxidative carbonylation of amine compounds, alcoholysis of urea and dimethyl carbonate ammonolysis.

① Reductive Carbonylation of Nitro Compounds

In 1988, Sergio Cenini et al. (Sergio Cenini, Corrado Crotti, Maddalena Pizzotti, Francesca Porta, Ruthenium carbonyl catalyzed reductive carbonylation of aromatic nitro compounds. A selective route to carbamates. *J Org. Chem.* 1988; 53(6):1243-50) stated the following: reacting 1,6-dinitrohexane organic nitro compounds, CO, $CH_3OH$ under the catalysis of noble metals such as palladium (Pd) or ruthenium (Ru) to obtain N,N'-dimethyl hexane-1,6-diyldicarbamate (HDU) followed by pyrolysis to form HDI and $CH_3OH$; the advantages of this process are mild reaction conditions and fewer byproducts. However, the method is disadvantageous since the noble metal catalysts should be recovered; the conversion of reactant, CO, is only ⅓, where it is difficult to separate the product, $CO_2$, from the reactant; and the reaction of $CO_2$ needs a high pressure, which is harsh and costly. The reaction scheme is shown below:

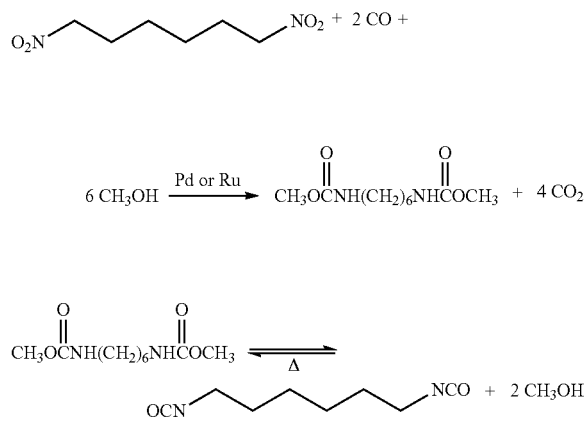

② Oxidative Carbonylation of Amine Compounds

In literature published by Fukuoka Shinsuke of Asahi Chemical Ind. (Japan) in 1985 (Fukuoka Shinsuke, Masazumi Chono, Masashi Kohno. A novel catalytic synthesis of carbamates by the oxidative alkoxycarbonylation of amines in the presence of platinum group metal and alkali metal halide or onium halide. J Org. Chem. 1984; 49(8):1458-60.), the reaction between hexanediamine, CO, $O_2$ and $CH_3OH$ was conducted in the catalysis of palladium (Pd) or potassium iodide (KI) to form N,N'-dimethyl hexane-1,6-diyldicarbamate (HDU), and subsequent pyrolysis of HDU provided HDI and $H_2O$. This method is advantageous in view of simplicity of the procedure together with higher conversion rate and selectivity. However, the disadvantage is a large amount of byproduct. The reaction scheme is shown below:

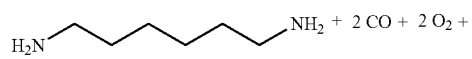

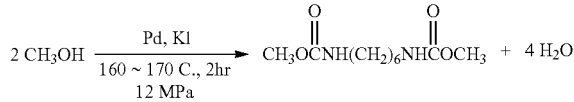

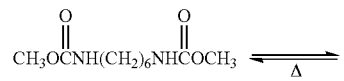

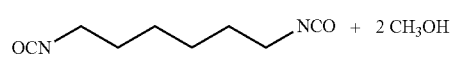

③ Alcoholysis of Urea

In 1986, a patent in the name of Franz of BASF (Germany) (U.S. Pat. No. 4,596,678 A) disclosed a reaction of hexanediamine, urea and $CH_3OH$ in the catalysis of metal salts of such as Li, Ca, Sn, Cu, etc. to form N,N'-dimethyl hexane-1,6-diyldicarbamate (HDU) and a subsequent pyrolysis of HDU that provided HDI and $CH_3OH$. The method generates an advantageously high yield of over 90% and can be comprehensively applied in the production of aliphatic isocyanates such as HDI/IPDP/H12MDI. However, the disadvantage is a longer process time for the reaction. The reaction scheme is shown below:

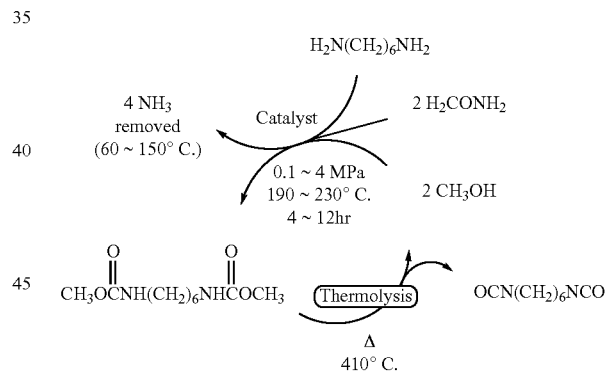

④ Dimethyl Carbonate Ammonolysis

In 2003, a patent in the name of Sergio (Spain) (U.S. Pat. No. 6,639,101 B2) disclosed a reaction of hexanediamine and dimethyl carbonate (DMC) under the catalysis of alkali or alkali earth group metals to form N,N'-dimethyl hexane-1,6-diyldicarbamate (HDU) and a subsequent pyrolysis of HDU that provided HDI and $CH_3OH$, where the byproduct $CH_3OH$ can be further reacted with CO and $O_2$ under oxidative carbonylation to form dimethyl carbonate (DMC) and $H_2O$ to achieve the goal of recycling and reusing the byproduct. The method has advantages in employing mild and environmentally friendly reaction conditions and recycling and reusing the byproduct. However, a large amount of byproduct is produced. In addition, the conversion of HDU to HDI needs a high pyrolysis temperature. The reaction scheme is shown below:

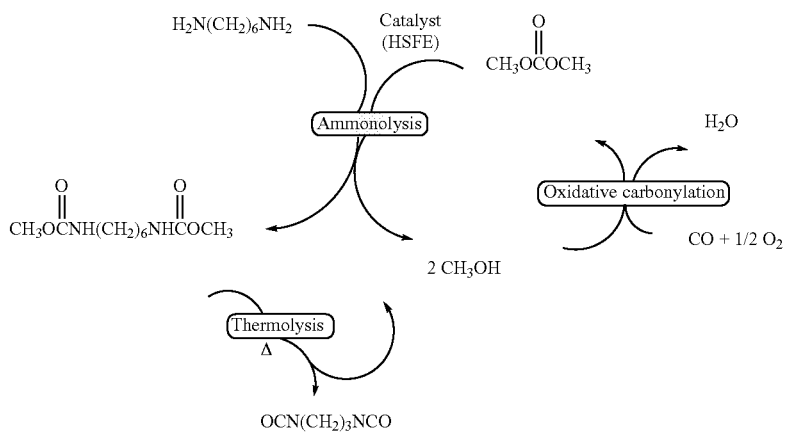

SUMMARY OF THE INVENTION

Given the above, the subject application provides a process for preparing aliphatic biscarbamates or aliphatic polycarbamates, comprising: reacting aliphatic diamine(s) or aliphatic polyamine(s) with diarylcarbonate in a solvent having low polarity to form at least one aliphatic biscarbamate or aliphatic polycarbamate, which can act as a precursor for the preparation of aliphatic diisocyanates or aliphatic polyisocyanates.

The subject application also provides a non-phosgene synthetic process for preparing aliphatic diisocyanates or aliphatic polyisocyanates, comprising: reacting aliphatic diamine(s) or aliphatic polyamine(s) with diarylcarbonate in a first solvent having low polarity to form aliphatic biscarbamate(s) or aliphatic polycarbamate(s), followed by thermolysis of aliphatic biscarbamate(s) or aliphatic polycarbamate(s) in a second solvent having low polarity to form aliphatic diisocyanates or aliphatic polyisocyanates, wherein the first solvent having low polarity is the same as or different from the second solvent having low polarity.

The subject application also provides a non-phosgene, one-pot process for preparing aliphatic diisocyanates or aliphatic polyisocyanates, comprising: reacting aliphatic diamine(s) or aliphatic polyamine(s) with diarylcarbonate in a second solvent having low polarity to form aliphatic biscarbamate(s) or aliphatic polycarbamate(s), followed by thermolysis of aliphatic biscarbamate(s) or aliphatic polycarbamate(s) in the same reactor to form aliphatic diisocyanates or aliphatic polyisocyanates.

Each embodiment or example of the subject invention as disclosed herein can be arbitrarily combined with any other; the subject application intends to cover all of the possible combinations.

In the specification and claims of the subject application, unless otherwise required by context, it will be understood that singular terms "a", "an" and "the" shall include plural forms of the same and plural terms shall include the singular. Unless otherwise required by context, all examples and the terms for describing exemplary embodiments (e.g. "such as") are used for well illustrating the invention but form no limitation of the invention. Any contents in the specification shall not be explained as identifying an essential element for carrying out the invention if the element is not claimed.

It should be understood that all numeric ranges referenced in this specification are intended to include all sub ranges included by the numeric ranges. For example, a range "from 50° C. to 70° C." includes all sub ranges between a minimum value 50° C. and a maximum value 70° C. (such as from 58° C. to 67° C., from 53° C. to 62° C., 60° C. or 78° C.), and includes the two end values 50° C. and 70° C. That is, a range in which a minimum value is greater than or equal to 50° C. and a maximum value is less than or equal to 70° C. is included. Since the disclosed numeric ranges are continuous, the numeric ranges include each value between a minimum value and a maximum value. Except for specific description, the numeric ranges specified in this specification are approximate values.

DETAILED DESCRIPTION OF THE INVENTION

Diarylcarbornates

The diarylcarbonates used in the subject application can be compounds represented by the following formula (1):

(1)

wherein $R^1$ and $R^2$ independently represent an aromatic group having 6 to 20, preferably 6 to 12 carbon atoms. When an aromatic group has two or more substituents, these substituents can be the same or different.

The substituents for $R^1$ and $R^2$ are preferably selected from alkyl or cycloalkyl having 1 to 12 carbon atoms, such as methyl, ethyl, propyl, butyl, etc.; arylalkyl having 7 to 15 carbon atoms, such as phenylmethyl, phenylethyl, etc.; aryl having 6 to 14 carbon atoms, such as phenyl, tolyl, etc.; alkoxyl having 1 to 12 carbon atoms, such as methoxyl, ethoxyl, propoxyl, butoxyl, trifluoromethoxyl, etc.; alkylthio having 1 to 12 carbon atoms, such as thiomethoxyl, thioethoxyl, etc.; aryloxyl having 6 to 14 carbon atoms, such as phenoxyl, etc.; halogen, such as fluoro, chloro, bromo, etc.; nitro; hydroxyl; cyano; and dialkylamino, such as dimethylamino, etc.

Substituted or unsubstituted $R^1$ and $R^2$ include, for example, phenyl, naphthalenyl, anthracenyl, tolyl, xylyl, ethylphenyl, propylphenyl, octylphenyl, nonylphenyl, dodecylphenyl, bisphenyl, methoxyphenyl, chlorophenyl, dichlorophenyl, trichlorophenyl, pentachlorophenyl, bromophenyl, dibromophenyl, tribromophenyl, pentabromophenyl, nitrophenyl, dinitrophenyl, hydroxylphenyl, cyanophenyl, dimethylaminophenyl, etc.

In addition, these aryls include ortho-, meta- and para-isomers, and the substituents linked to the aryls include n-, iso, sec- and tert-isomers.

In particular, diarylcarbonates having the same and unsubstituted aryl moieties can be selected from, but are not limited to, diphenyl carbonate, bis(1-naphthalenyl) carbonate, bis(2-naphthalenyl) carbonate and bis(9-anthracenyl) carbonate.

Diarylcarbonates having the same aryl moieties, wherein each of the aryl moieties is substituted by at least one alkyl, can be selected from, but are not limited to, bis(2-tolyl) carbonate and bis[4-(tert-butyl)phenyl] carbonate.

Diarylcarbonates having the same aryl moieties, wherein each of the aryl moieties is substituted by at least one aryl, can be selected from, but are not limited to, bis(4-bisphenylphenyl) carbonate.

Diarylcarbonates having the same aryl moieties, wherein each of the aryl moieties is substituted by at least one alkoxyl, can be selected from, but are not limited to, bis(2-methoxyphenyl) carbonate and bis(3-butoxyphenyl) carbonate.

Diarylcarbonates having the same aryl moieties, wherein each of the aryl moieties is substituted by at least one halogen, can be selected from, but are not limited to, bis(2-chlorophenyl) carbonate, bis(2,4-dichlorophenyl) carbonate and bis(2,4,6-trichlorophenyl) carbonate.

Diarylcarbonates having the same aryl moieties, wherein each of the aryl moieties is substituted by at least one nitro, can be selected from, but are not limited to, bis(2-nitrophenyl) carbonate and bis(2,4-dinitrophenyl) carbonate.

Diarylcarbonates having an unsubstituted aryl moiety and an aryl substituted by at least one alkyl can be selected from, but are not limited to, 3-tolyl phenyl carbonate and 4-tolyl phenyl carbonate.

Diarylcarbonates having an unsubstituted aryl moiety and an aryl substituted by at least one arylalkyl can be selected from, but are not limited to, 4-phenylmethyphenyl(phenyl) carbonate.

Diarylcarbonates having an unsubstituted aryl moiety and an aryl substituted by at least one alkoxyl can be selected from, but are not limited to, 4-methoxyphenyl phenyl carbonate and 4-ethoxyl-1-naphthalenyl phenyl carbonate.

Diarylcarbonates having an unsubstituted aryl moiety and an aryl substituted by at least one alkylthio can be selected from, but are not limited to 4-methylthiophenyl phenyl carbonate.

Diarylcarbonates having an unsubstituted aryl moiety and an aryl substituted by at least one aryloxy can be selected from, but are not limited to, 4-pheoxyphenyl phenyl carbonate.

Diarylcarbonates having an unsubstituted aryl moiety and an aryl substituted by at least one halogen can be selected from, but are not limited to, 2-chlorophenyl phenyl carbonate and 4-chlorophenyl phenyl carbonate.

Diarylcarbonates having an unsubstituted aryl moiety and an aryl substituted by at least one nitro can be selected from, but are not limited to, 3-nitrophenyl phenyl carbonate and 2,4-dinitrophenyl phenyl carbonate.

Diarylcarbonates having an unsubstituted aryl moiety and an aryl substituted by at least one hydroxyl can be selected from, but are not limited to, 3-hydroxyphenyl phenyl carbonate and 4-hydroxyphenyl phenyl carbonate.

Other diarylcarbonates suitable for use in the subject application include 4-methoxyphenyl-4'-nitrophenyl carbonate, 4-cyanophenyl-4'-nitrophenyl carbonate, 4-thiomethoxyphenyl-4'-nitrophenyl carbonate, 2-chlorophenyl-4'-nitrophenyl carbonate, 2-dimethylaminophenyl phenyl carbonate, 2-bromo-4-cyano-6-nitrophenyl phenyl carbonate and pentabromophenyl-2',4',6'-tribromophenyl carbonate.

Among the above-mentioned diarylcarbonates, it is preferable to use diphenyl carbonate, bis(2-tolyl) carbonate, bis(4-chlorophenyl) carbonate, bis(4-nitrophenyl) carbonate and bis(3,5-dimethoxyphenyl) carbonate, and more preferable to use diphenyl carbonate.

Aliphatic Diamines and Aliphatic Polyamines

The term "aliphatic" as used herein is intended to include aliphatic or aromatic-aliphatic moieties but not to include pure aromatic moieties.

Aliphatic diamines or aliphatic diamine compounds as used in the subject application comprise compounds represented by the following formula (2):

$$H_2N-R^3-NH_2 \quad (2)$$

Examples of $R^3$ comprise (but are not limited to) $C_{1-16}$ linear alkyl, such as methylene, dimethylene, trimethylene, tetramethylene, pentamethylene, hexamethylene, octamethylene and dodecamethylene; $C_{3-16}$ cycloalkyl, such as cyclopentyl, cyclohexyl, cycloheptyl, cyclooctyl, bis(cyclohexyl) and cyclooctyl substituted by alkyl; cycloalkyl substituted by alkyl, such as methylcyclopentyl, ethylcyclopentyl, methylcyclohexyl, ethylcyclohexyl, propylcyclohexyl, butylcyclohexyl, pentylcyclohexyl and hexylcyclohexcyl; $C_{3-16}$ cycloalkyl substituted by two (same or different) $C_{1-6}$ alkyls, such as dimethylcyclohexyl and diethylcyclohexyl; cycloalkyl substituted by three alkyls, such as 1,5,5-trimethylcyclohexyl, 1,5,5-triethylcyclohexyl, 1,5,5-tripropylcyclohexyl and 1,5,5-tributylcyclohexyl. In particular, aliphatic diamine compounds are preferably selected from butanediamines (BMDA), hexanediamines (HMDA), dodecanediamines (DMDA), cyclohexyldiamines, isophorone diamine and methylenedi(cyclohexyldiamine).

Aliphatic diamine compounds as used in the subject application may also comprise arylalkyldiamines, such as the compounds represented by the following formula (3):

$$H_2N-Ar-R^3-NH_2 \quad (3),$$

wherein Ar represents $C_{6-9}$ arylene; and $R^3$ is defined as above.

Arylalkyldiamines as used in the subject application can be those such as 4-(aminoethyl)phenylamine, etc.

Aliphatic polyamine compounds as used in the subject application refer to aliphatic hydrocarbons having three or more substituent amino groups, such as the compounds represented by the following formula (4):

$$R^4(NH_2)_p \quad (4),$$

wherein $R^4$ has the same definition of $R^3$ as stated above; and p represents an integer of at least 3.

Examples of aliphatic polyamine compounds as used in the subject application comprise propane-1,2,3-triamine, diethylenetriamine, bis(hexamethylene)triamine, triethylenetetraamine, 3-aminomethyl-1,6-hexanediamine and 1,3,6-triamino-n-hexane, etc. Aliphatic polyamine compounds as used in the subject application also comprise arylalkyl polyamines.

Solvents Having Low Polarity

Solvents having low polarity as recited in the subject application include a first solvent having low polarity and a second solvent having low polarity.

Solvents having low polarity as used in the subject application include low-polarity solvents and nonpolar solvents familiar to persons of ordinary skill in the art, in which the boiling point is preferably between 50° C. to 250° C., such as (but not limited to) ethers or alcohol ethers.

Ethers as used in the subject application are compounds having ether functionality, i.e., compounds having functionality of oxygen atom(s) bridging two moieties which are independently selected from alkyls and aryls. Ethers acting as solvents having low polarity in the subject application can be, for example, compounds represented by the following formula (5):

$R^5$ and $R^6$ independently represent $C_{1-9}$ alkyl, $C_{6-9}$ aryl or $C_{6-12}$ arylalkyl; or $R^5$, $R^6$ and the oxygen atom together form a ring ether having a ring moiety.

Ethers can be aryl ethers, aliphatic ethers, cycloaliphatic ethers or aromatic-aliphatic ethers. Examples of ethers include diethyl ether, anisole, diphenyl ether, tetrahydrofuran, 1,4-dioxane, etc.

Solvents having low polarity as used in the subject application also include alcohol ethers, comprising aromatic alcohol ethers, aliphatic alcohol ethers or aromatic-aliphatic alcohol ethers. Examples include glycol ethers, such as alkylene glycol ethers, for example alkylene glycol dialkyl ether, alkylene glycol aryl alkyl ether and alkylene glycol diaryl ether. Examples of alkylene glycol ethers include ethylene glycol ethers, which are the compounds represented by the following formula (6):

wherein $R^7$ and $R^8$ independently represent $C_{1-9}$ alkyl, $C_{6-9}$ aryl or $C_{6-12}$ arylalkyl; and a represents an integer from 1 to 3.

Preparation of Biscarbamates and Polycarbamates

Aliphatic biscarbamates or aliphatic polycarbamates are prepared from the aforementioned aliphatic diamines and diaryl carbonates in a first solvent having low polarity. This process allows efficient production and isolation of aliphatic biscarbamates or polycarbamates from aliphatic diamines or aliphatic polyamines at a low reaction temperature.

The first solvent having low polarity, as stated above, can be any solvent having low polarity as defined herein and preferably diethyl ether, anisole, diphenyl ether, tetrahydrofuran, 1,4-dioxane, ethylene glycol dimethyl ether, ethylene glycol diethyl ether, diethylene glycol dimethyl ether, triethylene glycol dimethyl ether, etc; more preferably diethyl ether, tetrahydrofuran, 1,4-dioxane, ethylene glycol dimethyl ether, ethylene glycol diethyl ether, diethylene glycol dimethyl ether, etc.

In one embodiment of the preparation process of aliphatic biscarbamates of the subject application, a ratio of aliphatic diamine compounds to diaryl carbonates from 1:2 to 1:5, preferably from 1:2 to 1:4 and more preferably from 1:2 to 1:3 is used.

In one embodiment of the preparation process of aliphatic biscarbamates of the subject application, a solute concentration from 20% to 100%, preferably 25% to 90% and more preferably 40% to 75%, such as about 50%, is used.

In one embodiment of the preparation process of aliphatic biscarbamates of the subject application, no metal catalyst is involved or a non-metal catalyst (such as carboxylic acid) is optionally used, and the carboxylic acid can be selected from the group consisting of benzoic acid, p-tert-butylbenzoic acid, p-anisic acid, isobutanoic acid, propanoic acid, butanoic acid and pivalic acid. When arylalkyldiamines are used as reactants, a non-metal catalyst is preferably used.

In the subject application, aliphatic biscarbamates can be efficiently prepared from aliphatic diamines and efficiently isolated at a low reaction temperature. For example, the reaction for producing biscarbamates is conducted at a temperature from 0° C. to 100° C., preferably from 15° C. to 100° C., more preferably from 15° C. to 60° C., such as from 15° C. to 25° C. or from room temperature to 60° C. In the preparation process of aliphatic biscarbamates of the subject application, after the reaction is completed, the target aliphatic biscarbamates precipitate from the reaction mixture and are collected. In the collection step, the reaction mixture is cooled to room temperature, or the temperature of the reaction mixture is controlled at about 40° C. or below, preferably from about 40° C. to about 0° C. and more preferably from about 30° C. to about 10° C. so that the aliphatic biscarbamates can precipitate from the reaction mixture and the precipitated aliphatic biscarbamates can be isolated by a separation means, such as filtration or centrifugation, and collected.

The thus-produced reaction mixture can be treated to isolate and collect the aliphatic biscarbamates. For example, the reaction mixture can be distilled to separate the reaction medium, carboxylic acids and phenolic compounds from the reaction mixture so that the residual solid substance can be directly collected; or the solid substance can be subjected to a further treatment, such as being washed by a solvent or being recrystallized, to isolate and collect aliphatic biscarbamates.

If necessary, after the filtration of aliphatic biscarbamates, the mother liquid can be subjected to a further treatment as mentioned above to advantageously recover more residual aliphatic biscarbamates from the mother liquid.

Upon filtration or centrifugation, distillation or washing with a solvent (such as toluene) can be optionally conducted to remove byproduct phenolic compounds and reaction medium from the mother liquid. In addition, after adding sufficient amounts of diaryl carbonates, amine compounds and optional catalysts into the mother liquid, the mother liquid can be reused in the preparation process of aliphatic biscarbamates of the subject application.

Even though the biscarbamates obtained by the process of the subject application exhibit a purity sufficient to be directly used in subsequent applications, recrystallization, if necessary, can be conducted to further refine the aliphatic biscarbamates. Solvents suitable for recrystallization include (but are not limited to) aromatic hydrocarbons (such as benzene, toluene and xylene), aliphatic alcohols (such as ethanol and n-butanol), ethers (such as bis(n-propyl) ether), esters (such as ethyl acetate, isobutyl acetate and cyclohecyl acetate) and ketones (such as methyl isobutyl ketone and cyclohexanone).

Two-Step Preparation Process for Diisocyanates or Polyisocyanates

The subject application also provides a non-phosgene thermolysis process for aliphatic diisocyanates or aliphatic polyisocyanates, comprising a step of thermolysis of aliphatic biscarbamates or aliphatic polycarbamates in a second solvent having low polarity.

The second solvent having low polarity used in the subject application, as stated above, can be any solvent having low polarity as defined herein. The first solvent having low polarity and the second solvent having low polarity can be the same or different. The second solvent having low polarity is preferably anisole, diphenyl ether, diethylene glycol dimethyl ether, triethylene glycol dimethyl ether, etc.

In one embodiment of the subject application, the biscarbamates obtained by the process of the subject application are subject to thermolysis in a second solvent having low polarity, which has a higher boiling point, to obtain diisocyanates. It is found that when the solvents having low polarity as defined herein are used, the removal of phenol (which is produced during heating) can be accelerated, while the formation of byproduct carbodiimides via dimerization of isocyanate products can be alleviated. The two effects are necessary for ensuring aliphatic products of HDI, IPDI, etc. transformed from precursor biscarbamates of HDI, DDI, IPDI, etc. at a high yield during the thermolysis process.

In the examples of the subject application, the thermolysis reaction means to convert aliphatic biscarbamates or aliphatic polycarbamates to corresponding diisocyanates (such as HDI, DDI, IPDI) or polyisocyanates and aromatic hydroxy compounds (such as phenol). In addition, upon the thermolysis reaction, diisocyanate or polyisocyanate products can be easily isolated from aromatic hydroxy compounds (such as phenol).

The second solvent having low polarity as used for the thermolysis reaction in the two-step process is preferably selected from those having a higher boiling point; for example, the compounds represented by formula (5) as stated above as ethers, where $R^5$ and $R^6$ independently represent $C_{6-9}$ alkyl, $C_{6-9}$ aryl or $C_{6-12}$ arylalkyl; or the compounds represented by either formula (5) or formula (6) where the boiling point is not less than the temperature for conducting the thermolysis reaction.

In another embodiment, the second solvent having low polarity as used for the thermolysis reaction in the two-step process has a higher boiling point than that of the first solvent having low polarity.

The temperature for thermolysis reaction is one sufficient to allow the biscarbamates or polycarbamates to thermolyze and depends on pressure, solvents, etc., such as a temperature ranging from 100° C. to 250° C. or 150° C. to 240° C. The pressure for the reaction can be a reduced pressure or a normal pressure, such as a pressure between 0.01 mmHg and 760 mmHg. When the byproduct phenol is constantly removed, the temperature for reaction can be a lower one.

There is no specific limitation of the time for reaction. Normally, the time for reaction is at most 3 hours, preferably from 0.5 to 2 hours and more preferably from 0.5 to 1 hour. In certain examples, when the process is conducted with a continuous or running system, the time for thermolysis reaction is significantly reduced to dozens of minutes or minutes for completion of the reaction.

One-Pot Process for Preparation of Diisocyanates or Polyisocyanates

The subject application also provides a non-phosgene one-pot process for aliphatic diisocyanates or aliphatic polyisocyanates, the process comprising reacting aliphatic diamine compounds or aliphatic polyamine compounds with diaryl carbonates followed by a thermolyzing step in the same reactor to prepare aliphatic diisocyanates or aliphatic polyisocyanates.

According to the aforementioned two-step process, the biscarbamates obtained in the first step have a sufficiently high purity, so the steps of synthesizing isocyanates and thermolyzing biscarbamates in the two-step process could be directly combined. Upon selecting suitable reaction conditions and solvents, diisocyanates or polyisocyanates can be obtained at a similar yield and purity to that obtained in the two-step process. The reaction conditions for the one-pot process for preparation of diisocyanates or polyisocyanates are generally the same as those used in the two-step process, but the former provides an advantage over the latter due to the elimination of the isolation step of biscarbamates or polycarbamates, thereby saving time and energy.

In the one-pot process for the preparation of diisocyanates or polyisocyanates, the second solvent having lower polarity is used, preferably one having a higher boiling point, such as the compounds represented by formula (5) as stated above as ethers, where $R^5$ and $R^6$ independently represent $C_{6-9}$ alkyl, $C_{6-9}$ aryl or $C_{6-12}$ arylalkyl; or the compounds represented by either formula (5) or formula (6) where the boiling point is not less than the temperature for conducting the thermolysis reaction.

The temperature for reaction in the one-pot process is one sufficient to allow biscarbamates or polycarbamates to form and thermolyze and depends on pressure, solvents, etc., such as a temperature ranging from 120° C. to 250° C., such as 240° C. The pressure for the reaction can be a reduced pressure or a normal pressure, such as a pressure from 0.01 mmHg to 760 mmHg. When the byproduct phenol is constantly removed, the temperature for reaction can be a lower one.

There is no specific limitation of the time for reaction. Normally, the time for reaction is at most 3 hours, preferably from 0.5 to 2 hours and more preferably from 0.5 to 1 hour. In certain examples, the time for conducting thermolysis reaction can be significantly reduced to dozens of minutes or minutes. For example, under a reduced pressure, the time for reaction can be 0.1 to 1 hour or 10 to 25 minutes.

Preparation of Polyurea

The subject application also provides a process of preparing polyurea directly from the aliphatic biscarbamates or polycarbamates with an amine compound or a mixture of amine compounds. In particular, polyurea can be prepared in a polar solvent by reacting the aliphatic biscarbamates or polycarbamates of the subject application with an amine compound or a mixture of amine compounds.

The amine compounds suitable for preparing the polyurea in the subject application can be selected from, but are not limited to, the group consisting of aliphatic or aromatic diamines having a long or short chain, which may be ether diamines, such as 1,8-diamino-3,6-dioxaoctane; long-chained polyether diamines, such as polyethoxylated or polypropoxylated diamines (D-2000); aliphatic diamines, such as 1,6-hexanediamine (1,6-HDA); cyclic aliphatic diamines, such as isophorone diamine (IPDA) and $H_{12}$MDA (hydrogenated MDA); and aromatic diamines, such as 4,4'-diaminodiphenylmethane (MDA).

Polar solvents suitable for use in the preparation of polyurea include, but are not limited to, N,N-dimethylacetamide (DMAc), N-methyl-pyrrolidone (NMP), dimethyl sulfoxide (DMSO) and tetramethylene sulfone (TMS), etc.

The temperature for reaction normally ranges from about 60° C. to about 200° C., preferably about 60° C. to about 160° C. and more preferably about 60° C. to about 100° C. The pressure for the reaction can be a reduced pressure, a normal pressure or an elevated pressure.

There is no specific limitation of the time for reaction. Normally, the time for reaction is from 0.001 to 100 hours, preferably from 0.005 to 50 hours and more preferably from 0.1 to 10 hours.

EXAMPLES

The invention of the subject application has been clearly and substantially described above and can be further illustrated by certain examples as provided below. These examples are provided merely for the purpose of illustration. Unless indicated otherwise, the examples are not intended to limit the claimed scope of the invention.

Example 1

Synthesis of 1,6-hexamethylene-bis(phenyl carbamates) (HMBPC)

Hexanediamine (HMDA, 6.0 g, 51.7 mmol) and diphenyl carbonate (DPC, 22.67 g, 106 mmol) were introduced into a 500 mL triple-neck flask containing 100 mL of ethylene glycol diethyl ether, and the mixture was stirred by a magnetic stirrer at room temperature. Nitrogen gas was introduced into the flask, while one neck of the flask was equipped with a thermometer and the other neck was connected to a condenser containing flowing water, where the top of the condenser was connected with an oil seal. The reaction was conducted for 2 hours. When the result of IR analysis indicated that 4,4'-diaminodiphenylmethane and monocarbamate intermediates no longer existed, the reaction was deemed complete.

After completion of the reaction, the reaction mixture was constantly stirred and the temperature of the reaction mixture was slowly lowered to room temperature. Precipitation of a white crystalline product was observed. Then, suction filtration was applied to isolate the product, and the product was dried in an oven under vacuum at 80° C. for 6 hours. White solid crystalline products were collected (17.53 g). 1H-NMR (200 MHz, d6-dimethyl sulfoxide) δ (ppm): 1.31 (s, 4H, —NHCH$_2$CH$_2$CH$_2$—), 1.45 (s, 4H, —NHCH$_2$CH$_2$—), 3.04 (s, 4H, —NHCH$_2$—), 7.06-7.36 (m, 10H, -Ph-), 7.73 (br s, 2H, —NH—). Yield: 98%. Melting point: 126.6° C.

Comparative Example 1

Based on the method disclosed in the patent (EP 2275405 A1) of Shinohata and Miyake under Asahi Kasei Chemicals Corp. (Japan), hexanediamine (HDA, 2.1 mol) was fed to a tank containing diphenyl carbonate (DPC, 6.3 mol) continuously at a rate of 200 g/hour and at 50° C., and excess phenol (10.5 mol) was used as a reaction solvent to conduct the reaction. 1,6-hexamethylene-bis(phenyl carbamates) (HMBPC) was obtained at a yield of 99.5% and subsequent thermolysis was conducted at about 180° C. The whole procedure of the process took an unduly long time (several days or even ten or so days). A simulated batchwise process was conducted based on the ratio of the reagents as disclosed in Asahi patent, where hexanediamine (HMDA, 6.0 g, 51.7 mmol) and diphenyl carbonate (DPC, 33.18 g, 155.1 mmol) were introduced into a 500 mL triple-neck flask containing 24.4 g of phenol (258.5 mmol). Upon stirring at 50° C., phenol in the reaction flask could not completely dissolve hexanediamine and diphenyl carbonate and the mixture was opaque and turbid. No further reaction was possible.

Then, the temperature was raised to 80° C. and 14.78 g of phenol was introduced simultaneously. Although the solid could be completely dissolved, the result of IR analysis at 16 hours showed that diphenyl carbonate and carbamate intermediates were still present in the reaction mixture, which means that the reaction was not finished.

Hsueh-Yung Chen et al. disclosed in their article (Hsueh-Yung Chen, Wen-Chen Pan, Chao-Hsing Lin, Chun-Ying Huang. Synthesis and trans-ureation of N,N'-diphenyl-4,4'-methylenediphenylene biscarbamate with diamines: a non-isocyanate route (NIR) to polyureas. J Polym Res 2012; 19: 9754.) using non-metal catalysts in the synthesis of biscarbamates; the full text is incorporated by reference herein. In particular, benzoic acid was introduced into the reactants and the final ratio between the raw materials HMDA/DPC/benzoic acid was 1/3/0.2 (51.7 mmol/155.1 mmol/10.3 mmol). After being stirred at 80° C. for 16 hours, the reaction mixture was slowly cooled to room temperature with continuous stirring. Precipitation of white crystalline products was observed. The product was isolated by suction filtration. Then, the thus-obtained product was washed with toluene (50 mL) and dried in an oven under vacuum at 80° C. for 6 hours. White solid crystalline products were collected and analyzed, and the result showed that 1,6-hexamethylene-bis(phenyl carbamates) (HMBPC) was obtained at a yield of 51.9% accompanied with 39.7% of urea byproduct.

Example 2

Synthesis of 1,6-hexamethylene-bis(phenyl carbamates) (HMBPC) with different solvents Phenol, toluene, methylcyclohexane, 1-bromopropane, ethylene glycol diethyl ether (1,2-diethoxyethane, EGDEE) were chosen as reaction solvents. The procedure and analysis as stated in Example 1 were conducted, where the conditions for synthesis were shown in Table 1. Results showed that ethylene glycol diethyl ether, a solvent having low polarity, was the best solvent, providing 1,6-hexamethylene-bis(phenyl carbamates) (HMBPC) at a highest yield of 90.3% accompanied with a lowest amount of 8.54% of byproduct urea.

TABLE 1

Effect on yield of product in the synthesis of HMBPC in view of solvents

| Composition | Solvent | Solute concentration (wt. %) | Reaction conditions | Yield of biscarbamates | Yield of urea |
|---|---|---|---|---|---|
| HMDA/ DPC/ Benzoic acid 1/3/0.2 | Phenol | 50% | 80° C./16 hr | 51.9% | 39.7% |
| | Toluene | 25% | 80° C./2 hr | 85.2% | 10.4% |
| | Methylcyclohexane | 25% | 100° C./2 hr | 86.1% | 10.9% |
| | 1-bromopropane | 25% | 45° C./2 hr | 88.0% | 11.5% |
| | Ethylene glycol diethyl ether | 25% | 45° C./2 hr | 90.3% | 8.54% |

Example 3

Synthesis of 1,6-hexamethylene-bis(phenyl carbamates) (HMBPC) with different amounts of diphenyl carbonate (DPC)

The same procedure and analysis done in Example 1 were repeated, but the amounts of diphenyl carbonate (DPC) shown in Table 2 were used. When the amount of diphenyl carbonate (DPC) were increased to 4-fold of HMDA (in mole), a highest yield of 95% of 1,6-hexamethylene-bis(phenyl carbamates) (HMBPC) and a lowest yield of 2.04% of byproduct urea were obtained.

TABLE 2

Effect on yield of product in the synthesis of HMBPC in view of the ratio of HMDA to DPC in ethylene glycol diethyl ether

| Composition | Solute concentration (wt. %) | Reaction conditions | Yield of biscarbamates | Yield of urea |
|---|---|---|---|---|
| HMDA/DPC/benzoic acid 1/4/0.2 | 25% | 25° C./2 hr | 95% | 2.01% |
| HMDA/DPC/benzoic acid 1/3/0.2 | 25% | 25° C./2 hr | 90.3% | 8.54% |

Example 4

Synthesis of 1,6-hexamethylene-bis(phenyl carbamates) (HMBPC) with different amounts of solute concentrations The same procedure and analysis done in Example 1 were repeated, but the solute concentrations shown in Table 3 were used. When the solute concentration (weight percent) was increased, the yield of 1,6-hexamethylene-bis(phenyl carbamates) (HMBPC) also increased, while the byproduct urea also increased. When the solute concentration was raised to 50%, a highest yield of 97.3% of 1,6-hexamethylene-bis(phenyl carbamates) (HMBPC) and a lowest amount of 1.49% of byproduct urea were obtained.

TABLE 3

Effect on yield of product in the synthesis of HMBPC in view of solute concentrations in ethylene glycol diethyl ether

| Composition | Solute concentration (wt. %) | Reaction conditions | Yield of biscarbamates | Yield of urea |
|---|---|---|---|---|
| HMDA/DPC/benzoic acid 1/4/0.2 | 100% | 100° C./2 hr | 97.2% | 4.01% |
| HMDA/DPC/benzoic acid 1/4/0.2 | 50% | 45° C./2 hr | 97.3% | 1.49% |
| HMDA/DPC/benzoic acid 1/4/0.2 | 25% | 25° C./2 hr | 95% | 2.04% |

Example 5

Synthesis of 1,6-hexamethylene-bis(phenyl carbamates) (HMBPC) in the absence of benzoic acid catalyst The same procedure and analysis done in Example 1 were repeated, but the amounts of diphenyl carbonate (DPC) and benzoic acid shown in Table 4 were used. In the cases that benzoic acid catalyst was not used, the byproduct urea was not formed even though the amount of diphenyl carbonate (DPC) decreased. When the amount of diphenyl carbonate (DPC) was decreased such that HMDA/DPC=1/2.05, a highest yield of 98% of 1,6-hexamethylene-bis(phenyl carbamates) (HMBPC) was obtained without generation of any urea byproduct during the reaction.

TABLE 4

Effect on yield of product in the synthesis of HMBPC in the absence/presence of benzoic acid catalyst in ethylene glycol diethyl ether

| Composition | Solute concentration (wt. %) | Reaction conditions | Yield of biscarbamates | Yield of urea |
|---|---|---|---|---|
| HMDA/DPC/benzoic acid 1/3/0.2 | 25% | 25° C./2 hr | 90.3% | 8.54% |
| HMDA/DPC 1/3 | 25% | 25° C./2 hr | 92.2% | 0% |
| HMDA/DPC 1/2.65 | 25% | 25° C./2 hr | 95% | 0% |
| HMDA/DPC 1/2.2 | 25% | 25° C./2 hr | 93% | 0% |
| HMDA/DPC 1/2.05 | 25% | 15° C./2 hr | 98% | 0% |

Example 6

Synthesis of Diphenyl N,N'-alkenylbiscarbamates under different diamines

The same procedure and analysis done in Example 1 were repeated, but the diamines shown in Table 5 were used. When a ratio of diamine/DPC of 1/2.05 and a solute concentration of 25% were utilized, corresponding diphenyl N,N'-alkenylbiscarbamates were obtained with respect to each diamine in a yield over 85%.

TABLE 5

Carbonylation on diamines for the preparation of N,N'-alkenylbiscarbamates in ethylene glycol diethyl ether

| Composition | Products | Yield of biscarbamates | Yield of urea | $T_m$ (° C.) | $T_d$ (° C.) |
|---|---|---|---|---|---|
| BMDA/DPC (1/2.05) | BMBPC | 89% | 0% | 162 | 162.8 |
| HMDA/DPC (1/2.05) | HMBPC | 98% | 0% | 126.6 | 147.4 |
| DMDA/DPC (1/2.05) | DMBPC | 98% | 0% | 122.5 | 181.6 |
| 4-(aminomethyl)aniline/ DPC/benzoic acid (1/4/0.2) | 4-TABPC | 85% | 0% | 170.8 | 171.8 |

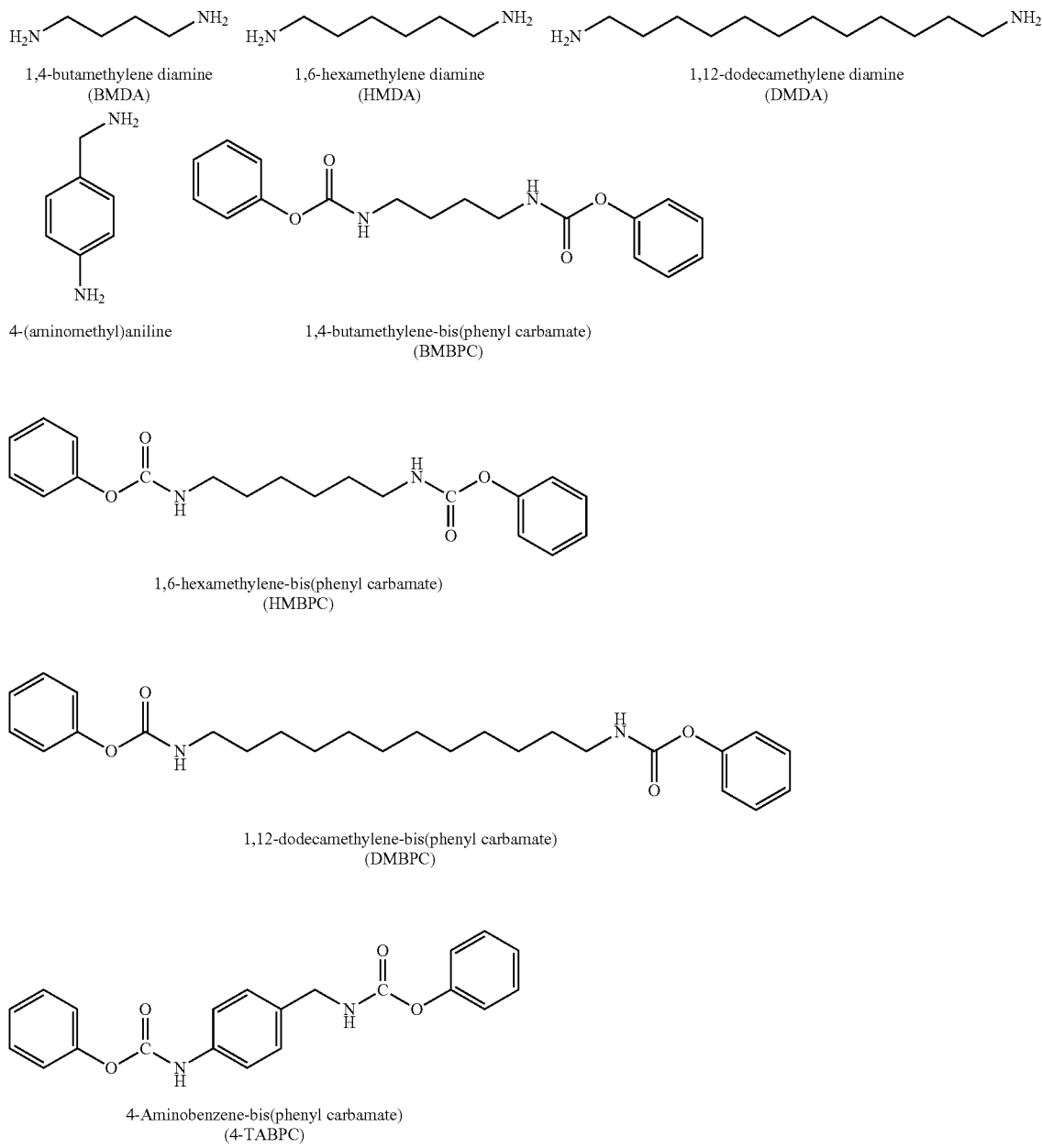

Structures of Diamines and N,N'-alkenylbiscarbamates 1,4-butamethylene diamine (BMDA)

1,6-hexamethylene diamine (HMDA)

1,12-dodecamethylene diamine (DMDA)

4-(aminomethyl)aniline 1,4-butamethylene-bis(phenyl carbamate) (BMBPC)

1,6-hexamethylene-bis(phenyl carbamate) (HMBPC)

1,12-dodecamethylene-bis(phenyl carbamate) (DMBPC)

4-Aminobenzene-bis(phenyl carbamate) (4-TABPC)

Example 7

Synthesis of 1,12-dodecamethylene diisocyanate (DDI) via thermolysis 1,12-dodecamethylene-bis(phenyl carbamate) (DMBPC, 27.78 g, 67.78 mmol) was introduced into a 500 mL triple-neck flask containing 250 g of diphenyl ether (the solute concentration was thus 10%), and the mixture was stirred by a magnetic stirrer upon heating from room temperature. Nitrogen gas was introduced into the flask, while one neck of the flask was equipped with a thermometer and the other neck was connected to a condenser containing flowing water, where the top of the condenser was connected with an oil seal. The reaction was conducted for 0.5 hour when the temperature reached 240° C. When the result of IR analysis indicated that 1,12-dodecamethylene-bis(phenyl carbamate) and intermediate monocarbamate no longer existed, the reaction was terminated.

After the reaction was terminated, the reaction mixture was continuously stirred and cooled to 100-150° C., and diphenyl ether was isolated via a vacuum pump from the product 1,12-dodecamethylene diisocyanate (DDI). It was observed that DDI was in transparent liquid form and the yield was 84%. The DDI was further treated by anhydrous methanol to block NCO groups, dried in a vacuum oven at 80° C. for 6 hours and analyzed to evaluate purity: 1H-NMR (200 MHz, d6-dimethylsulfoxide) $\delta$ (ppm) 1.21 (s, 8H, —NHCH2CH2CH2CH2-), 1.36 (s, 4H, —NHCH2CH2CH2CH2-), 2.92 (s, 4H, —NHCH2CH2CH2CH2-), 3.52 (s, 6H, CH3COO—NH—), 7.08 (m s, 2H, —NH—). Yield of DDI: 84%; recovery of phenol: 100%; recovery of diphenyl ether: 85%.

Synthesis of Diisocyanates from Diphenyl N,N'-Alkenylbiscarbamates Via Thermolysis The same procedure and analysis done in Example 7 were repeated but the diphenyl N,N'-alkenylbiscarbamates shown in Table 6 were used, and the corresponding diisocyanates also shown in Table 6 were obtained. When a solute concentration of 10% was applied, the products DDI and 4-IBPI were obtained in a yield of 84%.

Example 9

Preparation of 1,12-dodecamethylene diisocyanate (DDI) via one-pot process

Dodecanediamine (DMDA, 10 g, 50 mmol) and diphenyl carbonate (DPC, 21.9 g, 102.5 mmol) were introduced into a 500 mL triple-neck flask containing 96 g of diphenyl ether (the solute concentration was thus 25%), and the mixture was stirred by a magnetic stirrer at room temperature. Nitrogen gas was introduced into the flask, while one neck of the flask was equipped with a thermometer and the other neck was connected to a condenser containing flowing water, where the top of the condenser was connected with an oil seal. The reaction was conducted for 2 hours. When the result of IR analysis indicated that dodecanediamine and the intermediate monocarbamate no longer exist, the reaction was deemed finished. The reaction mixture was subsequently heated upon stirring with a magnetic stirrer in the same triple-neck flask, where nitrogen gas was introduced into the flask, one neck of the flask was equipped with a thermometer, the other neck was connected to a condenser containing flowing water, and the top of the condenser was connected with an oil seal. The reaction was conducted for 0.5 hour when the temperature reached 240° C. When the result of IR analysis indicated that 1,12-dodecamethylene-bis(phenyl carbamate) and the intermediate monocarbamate no longer existed, the reaction was terminated.

After the reaction was terminated, the reaction mixture was continuously stirred and cooled to 100-150° C., and diphenyl ether was isolated via a vacuum pump from the product 1,12-dodecamethylene diisocyanate (DDI). It was observed that DDI was in transparent liquid form and the yield was 80%. The DDI was further treated by anhydrous methanol to block NCO groups, dried in a vacuum oven at 80° C. for 6 hours and analyzed to evaluate purity: 1H-NMR (200 MHz, d6-dimethylsulfoxide) $\delta$ (ppm): 1.21 (s, 8H, —NHCH2CH2CH2CH2-), 1.36 (s, 4H, —NHCH2CH2CH2CH2-), 2.92 (s, 4H, —NHCH2CH2CH2CH2-), 3.52 (s, 6H, CH3COO—NH—), 7.08 (m s, 2H, —NH—). Yield of DDI: 84%; recovery of phenol: 100%; recovery of diphenyl ether: 85%.

Example 10

Preparation of Diisocyanates Via One-Pot Process

The same procedure and analysis proceeded in Example 9 were repeated but the diamines as shown in Table 7 were

TABLE 6

Diisocyanates prepared from biscarbamates via thermolysis in diphenyl ether solution

| Biscarbamate | Product | Solute concentration (wt. %) | Reaction conditions | Yield of diisocyanate | Recovery of phenol |
|---|---|---|---|---|---|
| BMBPC | 1,4-butamethylene diisocyanate (BDI) | 10% | 240° C./2 hr | 58% | 100% |
| HMBPC | 1,6-hexamethylene diisocyanate (HDI) | 10% | 240° C./2 hr | 76% | 100% |
| DMBPC | 1,12-dodecamethylene diisocyanate (DDI) | 25% | 240° C./0.5 hr | 84% | 100% |
| 4-TABPC | 1-isocyanate-4-(isocyanatomethyl)benzene | 5% | 240° C./1 hr | 84% | 100% | used, where the corresponding biscarbamates derived from the diamines were further thermolyzed in the same reactor to obtain the diisocyanates as shown in Table 7. When a solute concentration of 10% was applied, a product isophorone diisocyanate (IPDI) was obtained in a yield of 86%.

Table 7: One-Pot, Two-Stage NPR Process for the Preparation of Diisocyanates

| Product | Solute concentration (wt. %) | Reaction conditions | Yield of diisocyanates | Recovery of phenol | Recovery of diphenyl ether |
|---|---|---|---|---|---|
| 1,6-hexamethylene diisocyanate (HDI) | 5% | 240° C./ 1 hr | 70% | 100% | 85% |
| 1,12-dodecamethylene diisocyanate (DDI) | 25% | 240° C./ 0.5 hr | 80% | 100% | 100% |
| isophorone diisocyanate (IPDI) | 10% | 240° C./ 1 hr | 86% | 100% | 90% |

Structures of Diisocyanate Products

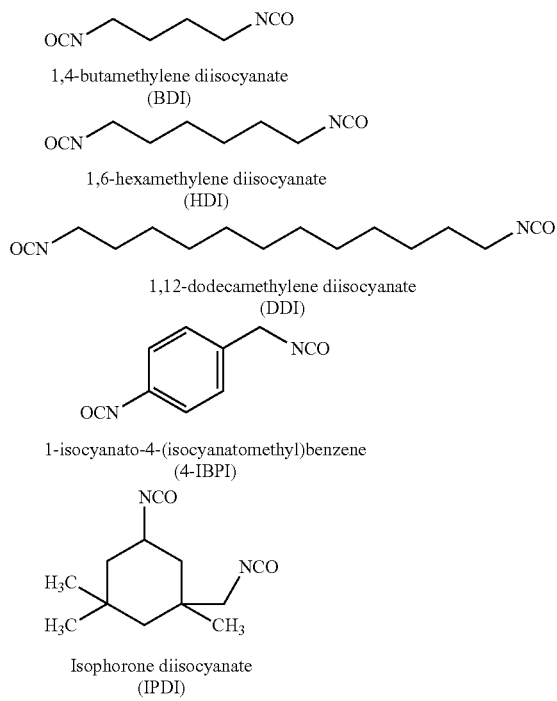

The examples above clearly indicate that aliphatic diisocyanates can be prepared under a high yield by a process involving a non-phosgene route (NPR), where aliphatic diphenyl N,N'-alkenylbiscarbamates act as reaction intermediates and are thermolyzed in mild reaction conditions and, in particular, in the absence of catalyst during the procedure.

In the preparation of biscarbamates, the yield of the product from carbonylation of diamines with diphenyl carbonate is highly affected by polarity of solvents. When a non-polar solvent (such as toluene or methylcyclohexane) is used, the rate of carbonylation is slower. On the other hand, when a solvent having high polarity (such as N-methyl-2-pyrrolidone (NMP) or N,N-dimethylacetamide (DMAc)) is used, the rate of carbonylation significantly increases but the amount of the byproduct urea also increases. For example, it was observed that using N-methyl-pyrrolidone in the preparation of biscarbamates at 80° C. only provided a yield of 52%, and the amount of the byproduct urea resulting from a further reaction of biscarbamates and amines significantly increased. Therefore, the inventors choose to use a solvent having low polarity (such as ethers or alcohol ethers) in the preparation of biscarbamates. It is preferred to use ethylene glycol diethyl ether (EGDEE) as a reaction solvent since the reaction can be completed within 2 hours at 25 to 40° C. and no urea byproduct is produced. In addition, biscarbamates can be obtained at a high purity by simple filtration after cooling the bulk to 25° C. for precipitation. The liquid mixture can be refined so that ethylene glycol diethyl ether (EGDEE) can be recovered up to an extent of 93% and reused in carbonylation in the preparation of biscarbamates.

Ethylene glycol diethyl ether (EGDEE) possesses a low dipole moment ($3\times10^{-6}$ Debye) and can well dissolve the mixture of amines and diphenyl carbonate at room temperature. In addition, the synthesis involving carbonylation can be conducted at 60° C. while the formation of the byproduct urea at a higher temperature can be prevented.

In the thermolysis of diphenyl N,N'-alkenylbiscarbamates for the preparation of aliphatic diisocyanates, non-polar hydrocarbon solvents such as n-dodecane (dipole moment=0) and several alkyl lubrication oils (dipole moment=0) were evaluated, which exhibit poor efficiency. Further analysis by HPLC indicated that the product contains oligomers such as isocyanurates. The result means that aliphatic diisocyanates are unstable in the solution (where n-dodecane acts as the solvent) when the temperature is over 200° C. during the synthesis procedure and oligomer byproducts are likely to be produced. On the other hand, using solvents having high polarity such as phenyl benzoate or dipolar solvents such as tetramethylene sulfone for thermolysis also yields poor result. In addition to the formation of deep yellow byproducts, the formation of trimers and carbodiimides seems to consume the desired product diisocyanates, resulting in an undesirably low yield.

The inventors found that solvents having low polarity, such as diphenyl ether, are preferable ones to be used in the thermolysis. Hence, it is disclosed to use solvents having low polarity in the thermolysis of aliphatic biscarbamates. Diphenyl ether is one of the suitable solvents since all aliphatic isocyanates can be isolated therefrom and phenol can be completely recovered. The reaction time is also significantly shortened. The result means that the incompatibility between the aromatic solvent, diphenyl ether (DPE), and aliphatic isocyanates is beneficial to bring the effect of azeotropic distillation and thereby aliphatic isocyanates can be isolated from the mixture. Moreover, no metal catalyst is used during the entire procedure.

Finally, the inventors design a novel one-pot and non-phosgene process based on the NPR route where "step 1" involves preparing biscarbamates and "step 2" involves thermolysis. For instance, 1,12-dodecanediamine (DMDA) could be carbonylated with diphenyl carbonate (DPC) in a diphenyl ether (DPE) solvent at 60° C. to prepare biscarbamates. At a solid content of 25%, the yield of biscarbamates (DMBPC) was nearly 100% while no urea byproduct was formed based on the analysis of infrared spectroscopy and HPLC. The solution was then directly heated to 240° C. for about 0.5 hours and the formation of 1,12-dodecamethylene diisocyanate and the disappearance of biscarbamates (DMBPC) were monitored by infrared spectroscopy. Finally, diphenyl ether (DPE) solvent was completely removed by distillation. The final product, 1,12-dodecamethylene diisocyanate (DDI, diisocyanate), could be isolated and the yield reached 80%, while the recovery of phenol also reached 100%. In comparison with the two-step process, one-pot NPR process is simpler while the product can be obtained at a comparable yield. This one-pot NPR process was also successfully applied to the preparation of isophorone diisocyanate from isophorone diamine at a yield reaching 86%.

In the subject invention, the non-phosgene route (NPR) processes in the preparation of aliphatic diisocyanate adopt several key principles in green chemistry and are well suited for the preparation of all aliphatic diisocyanates. Toxic carbonylation agents such as phosgene and metal catalysts are also avoided. In view of the advantages in safety and pollution, the non-phosgen route processes in the subject invention can replace current phosgen processes which are unsafe and toxic and can be applied in mass production of aliphatic diisocyanates at an industrial scale.

A person of ordinary skill in the art of the subject invention should understand that variations and modification may be made to the teaching and the disclosure of the subject invention without departing from the spirit and scope of the subject application. Based on the contents above, the subject application intends to cover any variations and modification thereof with the proviso that the variations or modifications fall within the scope as defined in the appended claims or their equivalents.

We claim:

1. A process for preparing aliphatic biscarbamates or aliphatic polycarbamates, the process comprising a step of reacting at least one aliphatic diamine or aliphatic polyamine with diaryl carbonate in a first solvent having low polarity to produce at least one aliphatic biscarbamate or aliphatic polycarbamate, the reaction optionally using a non-metal catalyst, and the first solvent having low polarity being ether or alcohol ether.

2. The process according to claim 1, wherein the diaryl carbonate is selected from the group consisting of diphenyl carbonate, bis(2-tolyl)carbonate, bis(4-chlorophenyl)carbonate, bis(4-nitrophenyl)carbonate and bis(3,5-dimethoxyphenyl)carbonate.

3. The process according to claim 1, wherein the aliphatic diamine or aliphatic polyamine is selected from the group consisting of butanediamines, hexanediamines, dodecanediamines, cyclohexyldiamines, isophorone diamine, 4-(aminoethyl)aniline, methylenedi(cyclohexyldiamine), propane-1,2,3-triamine, diethylenetriamine, bis(hexamethylene)triamine, triethylenetetraamine, 3-aminomethyl-1,6-hexanediamine and 1,3,6-triamino-n-hexane.

4. The process according to claim 1, wherein the first solvent having low polarity is selected from the group consisting of aryl ethers, aliphatic ethers, cycloaliphatic ethers, aromatic-aliphatic ethers, aromatic alcohol ethers, aliphatic alcohol ethers and aromatic-aliphatic alcohol ethers.

5. The process according to claim 4, wherein the first solvent having low polarity is selected from the group consisting of diethyl ether, tetrahydrofuran, 1,4-dioxane, ethylene glycol dimethyl ether, ethylene glycol diethyl ether, diethylene glycol dimethyl ether, triethylene glycol dimethyl ether, diphenyl ether and anisole.

6. The process according to claim 1, wherein the step is conducted at a molar ratio of aliphatic diamine or aliphatic polyamine to diaryl carbonate of 1:2 to 1:5.

7. The process according to claim 1, wherein the step is conducted at a solute concentration of 20 to 100% by weight.

8. The process according to claim 1, wherein no catalyst is used in the step.

9. The process according to claim 1, wherein the step is conducted at a temperature from 0 to 100° C.

10. The process according to claim 1, wherein the step is conducted at a reduced pressure.

11. A process for preparing an aliphatic diisocyanate or polyisocyanate, the process comprising:
a step of reacting at least one aliphatic diamine or aliphatic polyamine with diaryl carbonate in a first solvent having low polarity to produce at least one aliphatic biscarbamate or aliphatic polycarbamate, the reaction optionally using a non-metal catalyst, and the first solvent having low polarity being ether or alcohol ether; and
a step of thermolyzing the aliphatic biscarbamate or aliphatic polycarbamate in a second solvent having low polarity in the absence of a metal catalyst, wherein the second solvent having low polarity is selected from the group consisting of aryl ethers, aliphatic ethers, cycloaliphatic ethers, aromatic-aliphatic ethers, aromatic alcohol ethers, aliphatic alcohol ethers and aromatic-aliphatic alcohol ethers and is the same as or different from the first solvent having a low polarity.

12. The process according to claim 11, wherein the second solvent having low polarity is a compound represented by formula (5):

$$R^5—O—R^6 \quad (5),$$

wherein $R^3$ and $R^6$ independently represent $C_{6-9}$ alkyl, $C_{6-9}$ aryl or $C_{6-12}$ arylalkyl; or
a compound represented by formula (6):

$$R^7—(O—(CH_2)_2—)_aOR^8 \quad (6)$$

wherein $R^7$ and $R^8$ independently represent $C_{1-9}$ alkyl, $C_{6-9}$ aryl or $C_{6-12}$ arylalkyl; and
a represents an integer from 1 to 3.

13. The process according to claim 12, wherein the second solvent having low polarity is diphenyl ether, anisole, diethylene glycol dimethyl ether or triethylene glycol dimethyl ether.

14. The process according to claim 11, wherein the step is conducted at a temperature from 120 to 250° C.

15. The process according to claim 11, wherein the step is conducted at a reduced pressure.

16. A one-pot process for preparing an aliphatic diisocyanate or polyisocyanate, the process comprising a step of reacting at least one aliphatic diamine or aliphatic polyamine with diaryl carbonate in a second solvent having low polarity to produce at least one biscarbamate or polycarbamate and further thermolyzing the at least one biscarbamate or polycarbamate in the same reactor, wherein the second solvent having low polarity is selected from the group consisting of aryl ethers, aliphatic ethers, cycloaliphatic ethers, aromatic-aliphatic ethers, aromatic alcohol ethers, aliphatic alcohol ethers and aromatic-aliphatic alcohol ethers.

17. The process according to claim 16, wherein the diaryl carbonate is selected from the group consisting of diphenyl carbonate, bis(2-tolyl)carbonate, bis(4-chlorophenyl)carbonate, bis(4-nitrophenyl)carbonate and bis(3,5-dimethoxyphenyl)carbonate.

18. The process according to claim 16, wherein the aliphatic diamine or aliphatic polyamine is selected from the group consisting of butanediamines, hexanediamines, dodecanediamines, cyclohexyldiamines, isophorone diamine, 4-(aminoethyl)aniline, methylenedi(cyclohexyldiamine), propane-1,2,3-triamine, diethylenetriamine, bis(hexamethylene)triamine, triethylenetetraamine, 3-aminomethyl-1,6-hexanediamine and 1,3,6-triamino-n-hexane.

19. The process according to claim 16, wherein the second solvent having low polarity is a compound represented by formula (5):

$$R^5\text{—}O\text{—}R^6 \tag{5}$$

wherein $R^5$ and $R^6$ independently represent $C_{6-9}$ alkyl, $C_{6-9}$ aryl or $C_{6-12}$ arylalkyl; or a compound represented by formula (6):

$$R^7\text{—}(O\text{—}(CH_2)_2\text{—})_a OR^8 \tag{6}$$

wherein $R^7$ and $R^8$ independently represent $C_{1-9}$ alkyl, $C_{6-9}$ aryl or $C_{6-12}$ arylalkyl; and a represents an integer from 1 to 3.

20. The process according to claim 16, wherein the second solvent having low polarity is diphenyl ether, anisole, diethylene glycol dimethyl ether or triethylene glycol dimethyl ether.

21. The process according to claim 16, wherein the step is conducted at a molar ratio of aliphatic diamine or aliphatic polyamine to diaryl carbonate of 1:2 to 1:5.

22. The process according to claim 16, wherein the step is conducted at a solute concentration of 20 to 100% by weight.

23. The process according to claim 16, wherein no catalyst is used in the step.

24. The process according to claim 16, wherein the step is conducted at a temperature from 120 to 250° C.

25. The process according to claim 16, wherein the step is conducted at a pressure from 0.01 mmHg to 760 mmHg.

26. The process according to claim 16, the reaction being completed in a period from 0.1 to 1 hour.

27. The process according to claim 11, wherein the aromatic alcohol ethers, aliphatic alcohol ethers and aromatic-aliphatic alcohol ethers are selected from the group consisting of alkylene glycol dialkyl ethers, alkylene glycol aryl alkyl ethers and alkylene glycol diaryl ethers.

28. The process according to claim 16, wherein the aromatic alcohol ethers, aliphatic alcohol ethers and aromatic-aliphatic alcohol ethers are selected from the group consisting of alkylene glycol dialkyl ethers, alkylene glycol aryl alkyl ethers and alkylene glycol diaryl ethers.

* * * * *